(12) United States Patent
Schmitt

(10) Patent No.: US 8,348,669 B1
(45) Date of Patent: Jan. 8, 2013

(54) SURGICAL TEMPLATE AND METHOD FOR POSITIONING DENTAL CASTS AND DENTAL IMPLANTS

(75) Inventor: Stephen M. Schmitt, San Antonio, TX (US)

(73) Assignee: Bankruptcy Estate of Voxelogix Corporation, San Antonio, TX (US)

( * ) Notice: Subject to any disclaimer, the term of this patent is extended or adjusted under 35 U.S.C. 154(b) by 0 days.

(21) Appl. No.: 12/940,034

(22) Filed: Nov. 4, 2010

Related U.S. Application Data

(60) Provisional application No. 61/257,974, filed on Nov. 4, 2009.

(51) Int. Cl.
  *A61C 11/00* (2006.01)
  *A61C 13/10* (2006.01)
  *A61C 9/00* (2006.01)
(52) U.S. Cl. .................. 433/213; 433/196; 433/214
(58) Field of Classification Search ............ 433/24, 433/29, 54, 57, 72, 73, 196, 214, 213; 382/128
  See application file for complete search history.

(56) References Cited

U.S. PATENT DOCUMENTS

| | | | |
|---|---|---|---|
| 4,208,794 A | 6/1980 | Gerber | |
| 4,226,592 A | 10/1980 | Schreinemakers | |
| 4,234,307 A | 11/1980 | Draheim | |
| 4,251,215 A * | 2/1981 | May et al. .................. | 433/168.1 |
| 4,575,805 A | 3/1986 | Moermann et al. | |
| 4,615,678 A | 10/1986 | Moermann et al. | |
| 4,616,998 A | 10/1986 | Wong | |
| 4,766,704 A | 8/1988 | Brandestini et al. | |
| 4,795,345 A | 1/1989 | Ai et al. | |
| 4,837,732 A | 6/1989 | Brandestini et al. | |
| 4,859,181 A | 8/1989 | Neumeyer | |

(Continued)

FOREIGN PATENT DOCUMENTS

GB    2440267 A    1/2008

(Continued)

OTHER PUBLICATIONS

Schmitt, The 3rd Annual Eugene C. Gwaltney Manufacturing Symposium, "Rapid Prototyping for Product Development, Design, and Tooling: Making the New Technologies Pay Off for You" "Changing Peoples' Lives with RPM",Oct. 1-3, 1996, pp. 75-83 (10 pages).

(Continued)

*Primary Examiner* — Cris L Rodriguez
*Assistant Examiner* — Matthew Seward
(74) *Attorney, Agent, or Firm* — Cox Smith Matthews Incorporated

(57) ABSTRACT

A method is set forth for making a computer model of patient's jaws, face, teeth and removable dentures on the basis of digital information. Three dimensional digital data about the soft tissues, artificial teeth, supporting bone and position of nerves is combined in a virtual computer model to create an aesthetic and functional plan for the creation of surgical drill guides and the creation of new dentures and teeth. A key component of this method, the accurate positioning of dental casts in a physical articulator, is simplified using three dimensional virtual and physical measurements and movements. Surgical guides used to position dental implants are manufactured using computer milling, layered manufacturing or conventional laboratory techniques with the aid of mechanical tools that reproduce the position of the dental cast or digitally produced replica in the same orientation to the virtual implant position. This method eliminates the need to create radiographic templates of proposed restorations or damaging a patient's removable prosthesis to use it for imaging.

23 Claims, 11 Drawing Sheets

U.S. PATENT DOCUMENTS

| | | | |
|---|---|---|---|
| 4,901,737 A | 2/1990 | Toone | |
| 5,090,047 A | 2/1992 | Angotti et al. | |
| 5,237,998 A | 8/1993 | Duret et al. | |
| 5,257,203 A | 10/1993 | Riley et al. | |
| 5,409,017 A | 4/1995 | Lowe | |
| 5,501,598 A | 3/1996 | Misch | |
| 5,527,182 A | 6/1996 | Willoughby | |
| 5,588,430 A | 12/1996 | Bova et al. | |
| 5,605,459 A | 2/1997 | Kuroda et al. | |
| 5,652,709 A | 7/1997 | Andersson et al. | |
| 5,662,476 A | 9/1997 | Ingber et al. | |
| 5,690,843 A | 11/1997 | Schmitt et al. | |
| 5,697,997 A | 12/1997 | Aronsson et al. | |
| 5,725,378 A | 3/1998 | Wang | |
| 5,733,126 A | 3/1998 | Andersson et al. | |
| 5,741,215 A | 4/1998 | D'Urso | |
| 5,768,134 A | 6/1998 | Swaaelens et al. | |
| 5,779,477 A | 7/1998 | Boss | |
| 5,800,174 A | 9/1998 | Andersson | |
| 5,807,102 A | 9/1998 | Lang et al. | |
| 5,816,810 A | 10/1998 | Antonson et al. | |
| 5,823,778 A | 10/1998 | Schmitt et al. | |
| 5,829,981 A | 11/1998 | Ziegler | |
| 5,851,115 A | 12/1998 | Carlsson et al. | |
| 5,857,853 A | 1/1999 | Van Nifterick et al. | |
| 5,868,138 A | 2/1999 | Halstrom | |
| 5,871,358 A | 2/1999 | Ingber et al. | |
| 5,880,962 A | 3/1999 | Andersson et al. | |
| 5,885,077 A | 3/1999 | Jeffer | |
| 5,938,446 A | 8/1999 | Andersson et al. | |
| 5,951,289 A | 9/1999 | Kura et al. | |
| 5,967,777 A | 10/1999 | Klein et al. | |
| 5,971,760 A | 10/1999 | Letcher | |
| 5,975,893 A | 11/1999 | Chishti et al. | |
| 5,989,029 A | 11/1999 | Osorio et al. | |
| 5,993,214 A | 11/1999 | Persson | |
| 6,015,289 A | 1/2000 | Andreiko et al. | |
| 6,049,743 A | 4/2000 | Baba | |
| 6,055,986 A | 5/2000 | Meade | |
| 6,062,860 A | 5/2000 | Jorgenson | |
| 6,066,274 A | 5/2000 | Antonson et al. | |
| 6,082,995 A | 7/2000 | Wise | |
| 6,126,445 A | 10/2000 | Willoughby | |
| 6,149,433 A | 11/2000 | Ziegler et al. | |
| 6,152,731 A * | 11/2000 | Jordan et al. | 433/69 |
| 6,155,828 A | 12/2000 | Lazzara et al. | |
| 6,159,010 A | 12/2000 | Rogers et al. | |
| 6,168,435 B1 | 1/2001 | Beaty et al. | |
| 6,186,790 B1 | 2/2001 | Karmaker et al. | |
| 6,210,162 B1 | 4/2001 | Chishti et al. | |
| 6,217,325 B1 | 4/2001 | Chishti et al. | |
| 6,217,331 B1 | 4/2001 | Rogers et al. | |
| 6,223,067 B1 | 4/2001 | Vilsmeier et al. | |
| 6,227,851 B1 | 5/2001 | Chishti et al. | |
| 6,231,342 B1 | 5/2001 | Osorio et al. | |
| 6,261,098 B1 | 7/2001 | Persson | |
| 6,276,938 B1 | 8/2001 | Jorneus et al. | |
| 6,283,752 B1 | 9/2001 | Kumar | |
| 6,287,116 B2 | 9/2001 | Lazzara | |
| 6,287,119 B1 | 9/2001 | Van Nifterick et al. | |
| 6,296,483 B1 | 10/2001 | Champleboux | |
| 6,302,686 B1 | 10/2001 | Chott et al. | |
| 6,305,939 B1 | 10/2001 | Dawood | |
| 6,319,006 B1 | 11/2001 | Scherer et al. | |
| 6,322,359 B1 | 11/2001 | Jordan et al. | |
| 6,343,930 B1 | 2/2002 | Beaty et al. | |
| 6,354,836 B1 | 3/2002 | Panzera et al. | |
| 6,361,318 B1 | 3/2002 | Back et al. | |
| 6,382,975 B1 | 5/2002 | Poirier | |
| 6,394,801 B2 | 5/2002 | Chishti et al. | |
| 6,409,504 B1 | 6/2002 | Jones et al. | |
| 6,419,489 B1 | 7/2002 | Jorneus et al. | |
| 6,419,491 B1 | 7/2002 | Ricci et al. | |
| 6,431,866 B2 | 8/2002 | Hurson | |
| 6,463,344 B1 | 10/2002 | Pavloskaia et al. | |
| 6,491,723 B1 | 12/2002 | Beaty | |
| 6,505,625 B1 | 1/2003 | Uenishi | |
| 6,524,106 B1 | 2/2003 | Ziegler | |
| 6,530,375 B1 | 3/2003 | Cieslik, Jr. | |
| 6,540,516 B1 | 4/2003 | Ziegler | |
| 6,558,162 B1 | 5/2003 | Porter et al. | |
| 6,582,931 B1 | 6/2003 | Kois et al. | |
| 6,607,386 B1 | 8/2003 | Andersson et al. | |
| 6,621,491 B1 | 9/2003 | Baumrind et al. | |
| 6,633,789 B1 | 10/2003 | Nikolskiy et al. | |
| 6,640,150 B1 | 10/2003 | Persson et al. | |
| 6,648,645 B1 | 11/2003 | MacDougald et al. | |
| 6,652,765 B1 | 11/2003 | Beaty | |
| 6,655,962 B1 | 12/2003 | Kennard | |
| 6,665,570 B2 | 12/2003 | Pavloskaia et al. | |
| 6,671,539 B2 | 12/2003 | Gateno et al. | |
| 6,705,863 B2 | 3/2004 | Phan et al. | |
| 6,726,478 B1 | 4/2004 | Isiderio et al. | |
| 6,767,208 B2 | 7/2004 | Kaza | |
| 6,814,575 B2 * | 11/2004 | Poirier | 433/75 |
| 6,820,623 B2 | 11/2004 | Cook | |
| 6,886,566 B2 | 5/2005 | Eubank | |
| 6,935,861 B2 | 8/2005 | Lauciello | |
| 6,947,038 B1 | 9/2005 | Anh et al. | |
| 6,948,936 B2 | 9/2005 | Miller et al. | |
| 7,047,978 B2 | 5/2006 | Zuk | |
| 7,080,979 B2 | 7/2006 | Rubbert et al. | |
| 7,110,844 B2 | 9/2006 | Kopelman et al. | |
| 7,153,135 B1 | 12/2006 | Thomas | |
| 7,267,549 B2 | 9/2007 | Monkmeyer | |
| 7,286,954 B2 | 10/2007 | Kopelman et al. | |
| 7,322,824 B2 | 1/2008 | Schmitt | |
| 7,333,874 B2 | 2/2008 | Taub et al. | |
| 7,346,417 B2 | 3/2008 | Luth et al. | |
| 7,383,094 B2 | 6/2008 | Kopelman et al. | |
| 7,403,830 B2 | 7/2008 | Weber et al. | |
| 7,458,812 B2 | 12/2008 | Sporbert et al. | |
| 7,545,372 B2 | 6/2009 | Kopelman et al. | |
| 2001/0002310 A1 | 5/2001 | Chishti et al. | |
| 2003/0065259 A1 * | 4/2003 | Gateno et al. | 600/425 |
| 2003/0096210 A1 | 5/2003 | Rubbert et al. | |
| 2003/0215764 A1 | 11/2003 | Kopelman et al. | |
| 2004/0015176 A1 | 1/2004 | Cosman | |
| 2004/0152036 A1 | 8/2004 | Abolfathi | |
| 2004/0172150 A1 | 9/2004 | Perot et al. | |
| 2004/0172510 A1 * | 9/2004 | Nagashima et al. | 711/162 |
| 2004/0185422 A1 | 9/2004 | Orth et al. | |
| 2004/0219490 A1 | 11/2004 | Gartner et al. | |
| 2004/0229185 A1 | 11/2004 | Knopp | |
| 2004/0243481 A1 | 12/2004 | Bradbury et al. | |
| 2005/0084144 A1 | 4/2005 | Feldman | |
| 2005/0089822 A1 | 4/2005 | Geng | |
| 2005/0106528 A1 | 5/2005 | Abolfathi et al. | |
| 2005/0117693 A1 | 6/2005 | Miyano | |
| 2005/0136371 A1 | 6/2005 | Abolfathi et al. | |
| 2005/0153257 A1 | 7/2005 | Durbin et al. | |
| 2005/0163342 A1 | 7/2005 | Persky | |
| 2005/0170311 A1 | 8/2005 | Tardieu et al. | |
| 2005/0214716 A1 | 9/2005 | Weber et al. | |
| 2005/0244791 A1 | 11/2005 | Davis et al. | |
| 2005/0250075 A1 | 11/2005 | Taub et al. | |
| 2005/0271996 A1 | 12/2005 | Sporbert et al. | |
| 2006/0040236 A1 | 2/2006 | Schmitt | |
| 2006/0068355 A1 | 3/2006 | Schultz | |
| 2006/0111806 A1 | 5/2006 | Kraemer et al. | |
| 2006/0263738 A1 | 11/2006 | Kuo | |
| 2007/0031791 A1 | 2/2007 | Cinader, Jr. et al. | |
| 2007/0118243 A1 | 5/2007 | Schroeder et al. | |
| 2007/0134625 A1 | 6/2007 | Leu et al. | |
| 2007/0190481 A1 | 8/2007 | Schmitt | |
| 2007/0190488 A1 * | 8/2007 | Rusler | 433/171 |
| 2007/0190492 A1 | 8/2007 | Schmitt | |
| 2008/0020350 A1 | 1/2008 | Matov et al. | |
| 2008/0032257 A1 | 2/2008 | Muckler | |
| 2008/0064008 A1 * | 3/2008 | Schmitt | 433/140 |
| 2008/0085489 A1 * | 4/2008 | Schmitt | 433/75 |
| 2008/0102415 A1 | 5/2008 | Scott | |
| 2008/0227056 A1 * | 9/2008 | Bulard | 433/172 |
| 2008/0261168 A1 * | 10/2008 | Gutman et al. | 433/69 |
| 2010/0105002 A1 | 4/2010 | Karlsson et al. | |
| 2010/0106275 A1 | 4/2010 | Andersson et al. | |

FOREIGN PATENT DOCUMENTS

| WO | 2006031096 A1 | 3/2006 |
|---|---|---|
| WO | 2006096558 A2 | 9/2006 |
| WO | 2007079142 A2 | 7/2007 |
| WO | 2007084589 A2 | 7/2007 |
| WO | 2007084727 A1 | 7/2007 |
| WO | 2007130574 A1 | 11/2007 |
| WO | PCTUS07067424 | 1/2008 |
| WO | 2007062171 | 3/2008 |
| WO | PCTUS2007062171 | 8/2008 |

OTHER PUBLICATIONS

Schmitt, The 4th Annual Eugene C. Gwaltney Manufacturing Symposium, "Rapid Prototyping and Manufacturing: Applications in Product Development, Design and Tooling", "Changing Lives with RP", Georgia Institute of Technology, Oct. 1-2, 1997 pp. 21-26 (7 pages).

Bisler, et al., "The Virtual Articulator—Applying VR Technologies to Dentistry", Proceedings of the Sixth International Conference on Information Visualisation, IEEE Computer Society, 2002 (3 pages).

Üşümez, et al., "Inclinometer Method for Recording and Transferring Natural Head Position in Cephalometrics", American Journal of Orthodontics and Dentofacial Orthopedics, vol. 120, No. 6, Dec. 2001 pp. 664-670 (7 pages).

Kordaβ, et al., "The Virtual Articulator in Dentistry: Concept and Development", The Dental Clinics of North America, 46, 2002, pp. 493-506 (14 pages).

Murphy, et al., "The Development of Instrumentation for the Dynamic Measurement of Changing Head Posture", American Journal of Orthodontics and Dentofacial Orthopedics, vol. 99, No. 6, Jun. 1991, pp. 520-526 (7 pages).

Usumez, et al., "Effect of Complete Dentures on Dynamic Measurement of Changing Head Position: A Pilot Study", The Journal of Prosthetic Dentistry, vol. 90, No. 4, Oct. 2003, pp. 394-440 (7 pages).

Üşümez, et al., "Reproducibility of Natural Head Position Measured with an Inclinometer", American Journal of Orthodontics and Dentofacial Orthopedics, vol. 123, No. 4, Apr. 2003, pp. 451-454 (4 pages).

Delli, "Automated Design and Fabrication of Dental Bar", University of Missouri-Rolla, Nov. 17, 2006 (23 pages).

Leu, et al., "Computer-Automated Dental Bar Design", Technology/Business Opportunity, University of Missouri-Rolla, no date (2 pages).

Gawate, "Dental Bar Design (Thesis)", University of Missouri, Published 2005 (67 pages).

Taylor, "Influence of Computerized Tomography Parameters on the Quality of Stereolithographic Models (Thesis)". The University of Texas Graduate School of Biomedical Sciences, Mar. 1999 (102 pages).

Verstreken et al. "An Image-Guided Planning System for Endosseous Oral Implants" Oct. 1998, IEEE Transactions on Medical Imaging, vol. 17, No. 5, pp. 842-852 (11 pages).

* cited by examiner

SURGICAL TEMPLATE AND METHOD FOR POSITIONING DENTAL CASTS AND DENTAL IMPLANTS

CROSS-REFERENCE TO RELATED APPLICATIONS

This application claims priority under 35 U.S.C. §119 (e) to U.S. Provisional Patent Application No. 61/257,974 filed Nov. 4, 2009, the disclosure of which is incorporated herein by reference.

FIELD

The present application generally relates to a dental apparatus and method, and more particularly to methods of orienting dental casts in an articulator based digital models, and the construction of devices using such techniques.

BACKGROUND

Many methods of planning and guiding the proper position of dental implants have been revealed. Frequently a radiographic template is made to fit to the patient's teeth, and radiographic markers are attached to the template. Klein (U.S. Pat. No. 5,967,777) revealed a method that uses a plastic replica of the prospective teeth to be supported by dental implants. This is a time consuming process since a dental laboratory technician must set or carve teeth to fit in the ideal position for a given patient. The patient is then scanned with the radiographic template, preferably using computed tomography (CT). If the patient has teeth that will be removed at the time of implant placement, it is difficult to image these areas since the teeth are still present and radiographic scatter frequently makes it difficult to determine the actual shape of the teeth. It is also difficult to position the template in a predictable position after the teeth to be removed. Other methods have been revealed that require the patient's teeth be removed first and removable dentures made.

The NobelGuide™ (Nobel Biocare) system uses this technique. After healing, radiographic markers are placed in the dentures and the patient is imaged using CT. A second scan of the patient's denture is made of the denture alone, and then the radiographic markers are used to align the two CT scans in the same computer space. The Nobel system allows for planning of the dental implant position in relation to the patient's denture and the supporting bone, but it requires that the patient's dentures be damaged by placing gutta percha markers in the plastic to align the images. If the dentures are not used, then they are duplicated to make a new set with radiographic markers. Generally, the duplicate set is less accurate, which involves an additional cost and source of errors.

Thus, there is a need for an improved method of imaging a patient and planning for implant placement that provides for the virtual positioning of artificial teeth in harmony with the patient's facial structure and appearance and the virtual positioning of implants in relation to the remaining bone. There is also a need for a method of communicating this information easily to the surgeon, restorative dentist and laboratory. It is also desirable that changes can be made in the virtual plan such that the surgeon, restorative dentist or laboratory can modify the treatment plan as needed.

SUMMARY

A method of positioning a model of a patient's dentition may comprise receiving first digital data representative of a patient's dentition; receiving CT data of the patient's fossae and a CT bite plate having three or more non-linear radiographic markers, said dentition being oriented with respect to said fossae in an actual orientation, said CT bite plate being engaged with said dentition; creating a virtual model of said dentition, said fossae, and said radiographic markers from said first digital data and said CT data, said virtual model comprising a virtual representation of said dentition, a virtual representation of said fossae, and a virtual representation of said radiographic markers, wherein said virtual representation of said dentition is oriented with respect to said virtual representation of said fossae in a virtual orientation, said virtual orientation being substantially the same as said actual orientation; mounting an actual model of said dentition in a positioning device using said CT bite plate, said positioning device comprising a removable mounting plate, said mounting plate being attachable to an actual articulator in a known orientation; orienting said actual model of said dentition with respect to said mounting plate in said positioning device; attaching said actual model to said mounting plate; removing said actual model and said mounting plate from said positioning device; and positioning said actual model in said actual articulator using said mounting plate.

U.S. patent application Ser. No. 11/674,956 entitled Method of Making a Virtual Computer Model of the Jaws, which is herein incorporated by reference, reveals a method of using computed tomography (CT) to image the hard and soft tissues of the head and neck. It also reveals a method of imaging dental casts of a patient using non-radiographic techniques to eliminate radiographic scatter caused by dental restorations in CT scans.

U.S. patent application Ser. No. 11/739,310 Computer Milled Dental Tooth System, which is herein incorporated by reference, reveals a method of tracking the positional relationship of the upper and lower jaws with static records (wax bites), average measurements, and a digital recording device called ARCUSdigma digital recorder (KAVO Company). It also reveals a method of virtually positioning artificial denture teeth and using computer milling to shape the teeth and the dental cast to construct immediate dentures using digital technology.

U.S. patent application Ser. No. 11/851,105 Method and Process for the Virtual Design and Computer Manufacture of Intra Oral Devices, which is herein incorporated by reference, reveals a method of imaging dental casts, recording spatial relationships, and creating virtual movement of the models such that actual devices can be made with computer technology.

U.S. patent application Ser. No. 11/867,590, Surgical Guides and Method for Positioning Artificial Teeth and Dental Implants, which is herein incorporated by reference, reveals methods of evaluating and treating a patient's anatomy prior to tooth removal and planning ideal position of artificial teeth. It also is directed to methods for the computer manufacturing of artificial teeth attached to dental implants.

U.S. Pat. No. 7,322,824 issued Jan. 29, 2008, and U.S. patent application Ser. No. 12/048,047 filed Mar. 13, 2008 and Ser. No. 12/208,163 filed Sep. 10, 2008 are incorporated herein by reference.

The methods and apparatus taught in the foregoing applications and patent may be used as a basis for creating virtual models as described herein.

In some embodiments, methods are presented to create a digital image of a patient using the patient's existing teeth or removable dentures to record the spatial orientation of the jaws and shape of the soft tissues in relation to the supporting bone without damaging or altering the dentures or natural teeth.

In some embodiments, methods are presented for positioning physical dental casts or digital replicas of dental casts in an articulator in the same spatial orientation to the patient's rotational centers, planned incisal edge position, and anatomic planes as existed in the digital imaging.

In some embodiments, methods are presented to create a virtual computer model of a patient's mouth and to ideally position virtual artificial teeth in proper spatial orientation to the supporting tissues, teeth, and the opposing arch. The positioning of teeth may be determined by the use of virtual planes, curved surfaces, or other digital references.

In some embodiments, methods are presented to virtually determine the ideal position to place implants in the remaining supporting bone.

In some embodiments, methods are provided for the restorative dentist, surgeon, and laboratory to communicate and change, if needed, the actual 3D virtual plan for any given patient via the Internet.

In some embodiments, methods are provided to use advanced computer manufacturing techniques (e.g., milling and layered manufacturing) to make drill guides, immediate dentures, and immediate load prostheses with minimal manual labor.

In some embodiments, methods are provided to use mechanical positioning devices to reproduce the spatial orientation of the dental cast or replica of the dental cast to the virtual dental implant position and to use conventional laboratory techniques to make the surgical template.

In some embodiments, methods are provided for evaluating the aesthetic appearance of a patient prior to tooth removal and to use virtual techniques that allow for the selection of ideal replacement teeth, shaping the supporting bone, placing implants, construction of surgical guides and immediate prosthesis all via the Internet such that many individuals in different parts of the world can communicate and support the process of planning and treating patients that require implant therapy.

DETAILED DESCRIPTION

The term "dental cast" as used herein means a structure composed of any material that is shaped to model a patient's natural teeth or denture. A dental cast may correspond to the upper jaw, the lower jaw or both.

Figure 1:
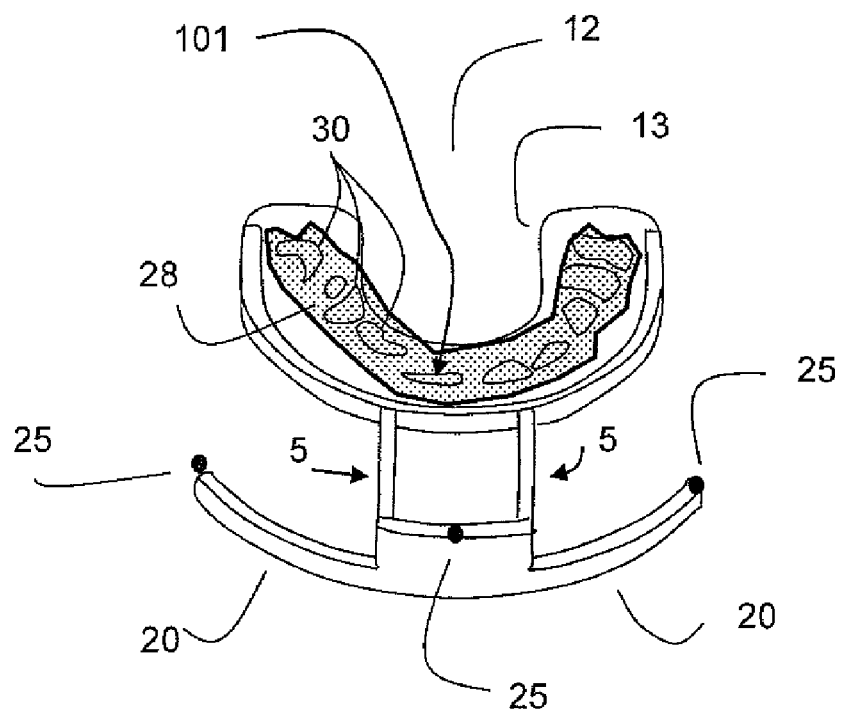
FIG. 1 depicts a CT bite plate.
Figure 3:
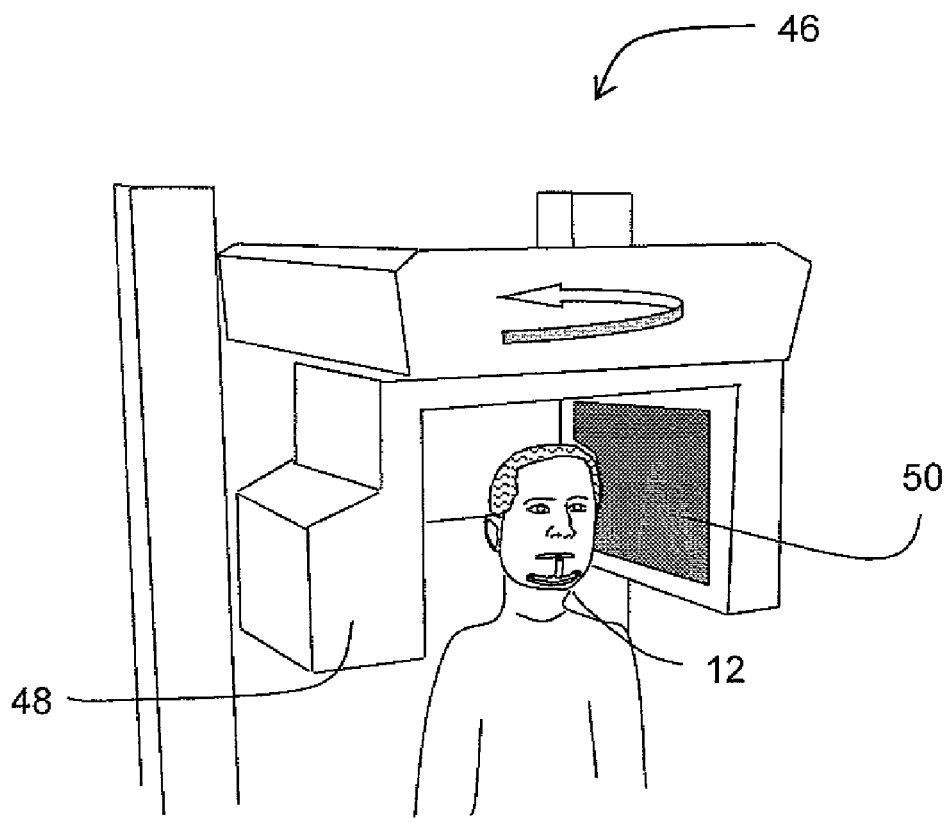
FIG. 3 illustrates a patient being imaged in a CT scanner

FIG. 1 illustrates a CT bite plate assembly 12. The bite plate assembly 12 has a U-shaped rigid section attached to a thin bite surface 13 made of a radiolucent material that will mate with the patient's teeth and yet have minimal opening of the jaws. The assembly 12 has central forward projections 5 that extend between the lips when the assembly is placed in the mouth. The forward projections 5 join a vertical portion that extends above or below the plane of occlusion. Wings 20 extend laterally from the vertical portion and generally follow the contour of the face but do not contact it. Three or more non-linear radiographic markers 25 are attached to the vertical and wing portions of the CT bite plate. These markers have a radiographic density that makes them visible in CT data, such as may be collected as shown in FIG. 3, and also have a geometric shape that can be converted to a digital image with non-radiographic imaging, including for example contact, light, laser, or holographic techniques. Bite registration material 28 records the indentations 30 of any of the upper and lower teeth of a patient, or of a denture, when the patient bites into the CT bite plate. Note the indentation 101 made by one of a patient's incisor teeth, or associated portion of a denture. The indentation 101 may, as described below, become associated with a virtual image of an incisor and may be a useful reference point for movement of a virtual model as discussed with respect to FIG. 4B.

Figure 2A:
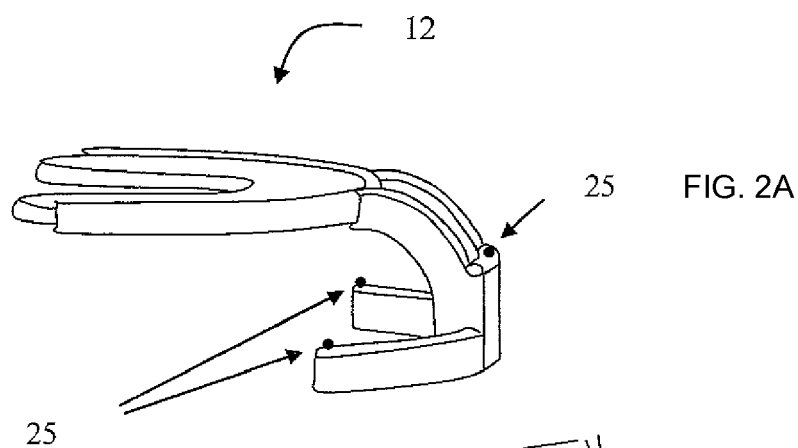
FIG. 2A illustrates a CT bite plate.
Figure 2B:
FIG. 2B illustrates the CT bite plate in the patient's mouth positioned between removable dentures.
Figure 2C:
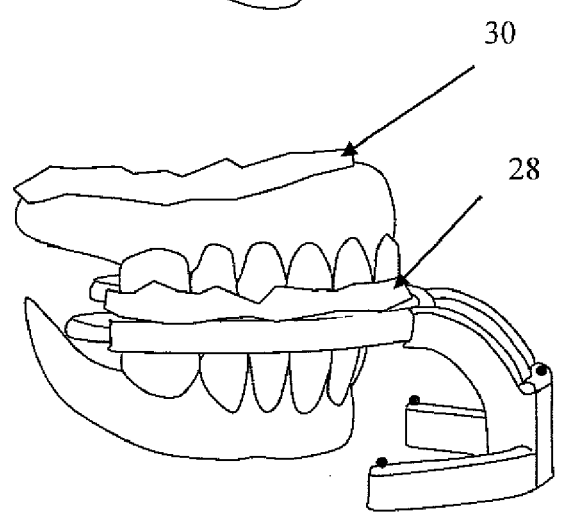
FIG. 2C illustrates a CT bite plate attached to dentures.

FIG. 2A illustrates the CT bite plate assembly 12 with radiographic markers 25. FIG. 2B illustrates the CT bite plate assembly positioned between the patient's dentures in his mouth. FIG. 2C illustrates that the dentures can be altered with impression material 30 to provide a better adaptation to the soft tissues and shape for new dentures. In some embodiments, bite registration material 28 may be placed on the CT bite plate to record the position of the patient's existing teeth or dentures and jaws using a CT scan. In some embodiments, bite registration material 28 may be placed on the CT bite plate to record the position of the patient's existing teeth or denture and jaws using non-radiographic means.

FIG. 3 illustrates a CT bite plate 12 placed in the patient's mouth and the patient positioned in a CT machine 46. An x-ray source 48 projects radiation across the patient's head and is detected on a sensor 50.

In some embodiments, in addition to the CT scan data collected as shown in FIG. 3 a second scan using, for example, non-radiographic techniques may be made. Non-radiographic techniques may include, for example and without limitation, contact, light, laser, or holographic imaging. The second scan may be made of the dentures or a dental cast wherein the CT bite plate is disposed outside of the patient's mouth to record the patient's occlusal and tissue surfaces. The two scans can then be aligned in a computer model using the radiographic markers 25. Such techniques are described in more detail in U.S. patent application Ser. No. 11/851,105, of which Applicant is the sole inventor.

Imaging an impression of the patient's existing teeth or denture and the CT bite plate may be performed in a manner that does not damage the denture, any existing teeth, or both. In some embodiments, the undamaged denture may be returned to the patient. In some embodiments the denture and any impression material may be altered, such as by injecting a contrast agent into either the denture or the impression material.

Figure 4A:
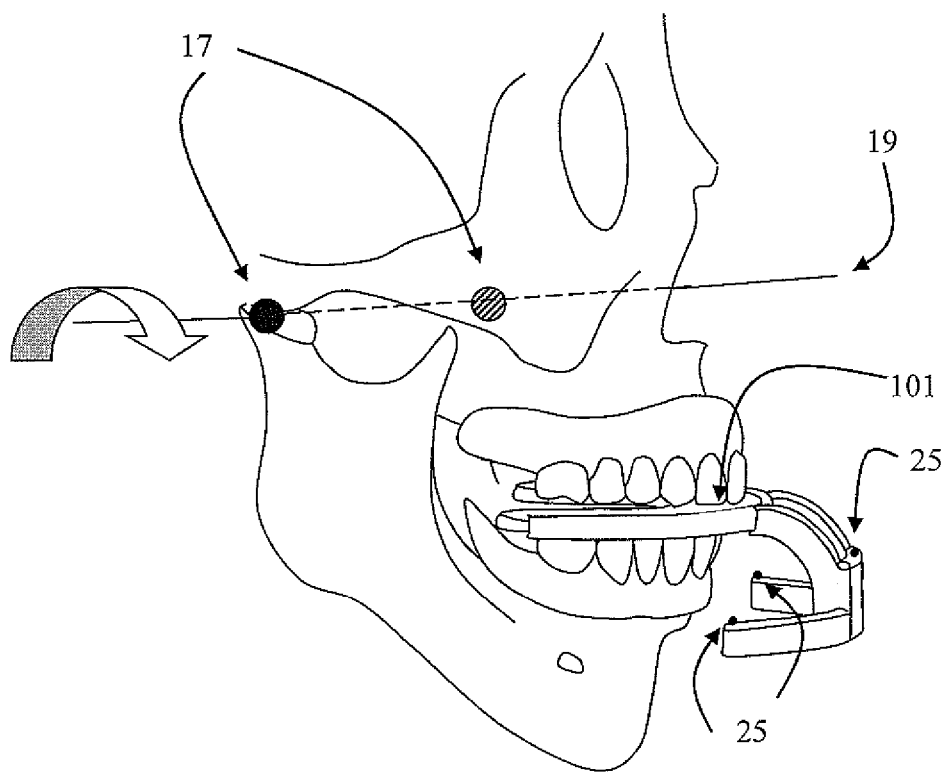
FIG. 4A is a side perspective view that illustrates the three dimensional rendering of CT data locating radiographic markers, rotational centers, and anatomical markers for the ideal placement of teeth.

FIG. 4A illustrates the 3D rendering of the CT data to record the shape of bone, dentition, CT bite plate, radiographic markers 25, rotational centers 17 and axis of rotation 19. The rotational centers 17 are identified using 3D data such as the skin and tragus of the ear, external auditory meatus, condylar head, condylar fossae or actual digital recording of the axis points. The location of the incisor tooth before treatment can also be located from the indentation 101 on the CT bite plate or in the CT data.

Figure 4B:
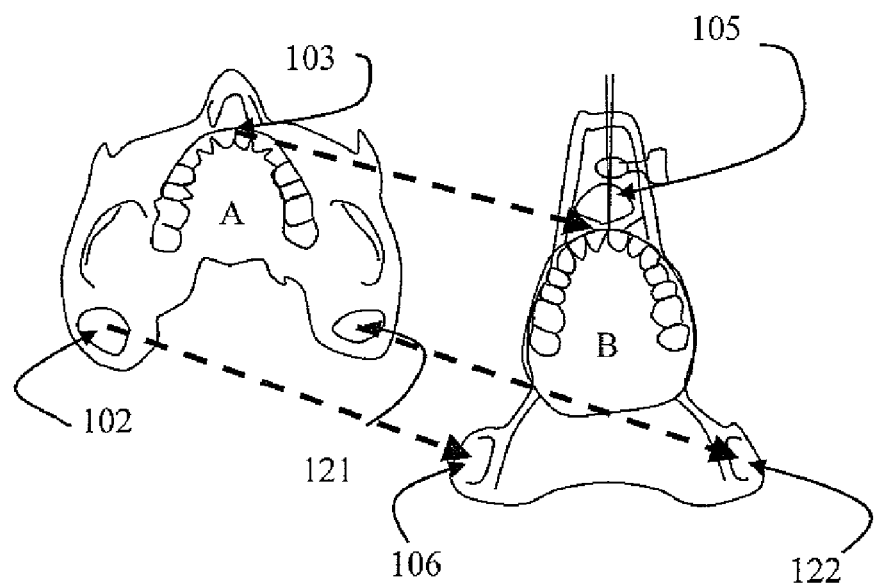
FIG. 4B is a coronal view that illustrates alignment of a virtual image of upper teeth and boney structures to a corresponding position and boney structures in a virtual representation of an articulator.

FIG. 4B is a coronal view and illustrates the alignment of data representing a virtual image of the upper teeth and upper boney structures A to the precise corresponding position and boney structures in a virtual representation of an articulator B. The alignment of a virtual image of the upper teeth and upper bony structures to the virtual articulator may be accomplished using related points. For example, point 102 may be a virtual representation of the left fossae in the virtual image of the upper teeth and upper boney structures A and may relate to point 106, a virtual representation of the left mechanical fossae, in a virtual representation of an articulator. Point 121 may be a virtual representation of the right fossae in the virtual image of the upper teeth and upper boney structures A and may relate to point 122, a virtual representation of the right mechanical fossae, in a virtual representation of an articulator. Thus, the virtual model may include the locations of the anatomic fossae. Point 103 may be a virtual representation of the incisor and may relate to point 105, a virtual representation of the vertical position of the incisal pointer, in the virtual representation of an articulator. Ideally, at least three related points may be used to align a virtual image of the upper teeth and upper boney structures A to the precise corresponding position of a virtual representation of an articulator B.

Once a virtual image of the upper teeth and upper boney structures is oriented with a virtual representation of the articulator, the virtual data of either object may be modified in any number of ways, including for example, by translation or rotation, and modification of the other object may be correlated. In some embodiments, an origin point, located in three dimensional space, may be used to relate translation or rotation of a virtual object. In some embodiments, the alignment of data representing a virtual image of the upper teeth and upper boney structures A to the precise corresponding position and boney structures in a virtual representation of an articulator B (as shown in FIG. 4B) may be followed by defining a common origin point for both objects. In some embodiments, a common origin point may be related to two virtual objects, and the trigonometric relationship of the common origin points may be known with regards to the reference points for an object and markers, including radiographic markers 25. In some embodiments, motion of a virtual object may be correlated with movement of the physical object represented by that virtual object through knowledge of the physical location of radiographic markers 25. For example, as further shown below in FIG. 6, three non-linear markers 25 are shown, and those markers 25 may serve to relate data in virtual space to physical objects.

Figure 4C:
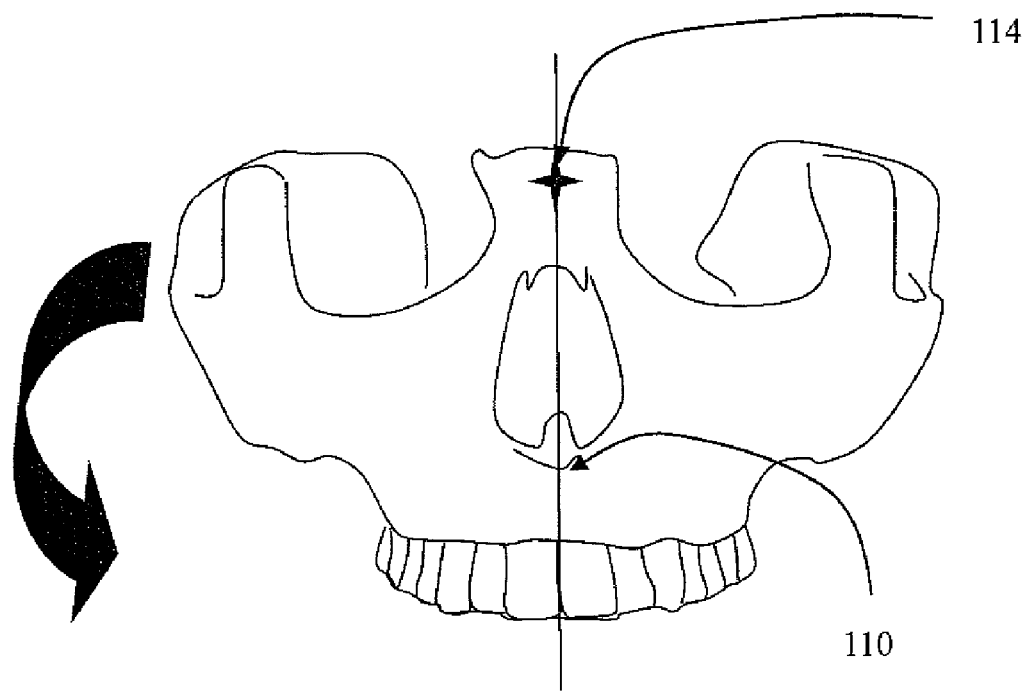
FIG. 4C is a frontal view of virtual image data that illustrates a nasion point and an anterior nasal spine point.

FIG. 4C is a frontal view of the virtual image data showing the nasion point 114 and the anterior nasal spine point 110 from the CT data. This data may be rotated in the frontal plane of the virtual representation of an articulator around the anterior nasal spine to position the nasion in a vertical position directly over the anterior nasal spine.

Figure 4D:
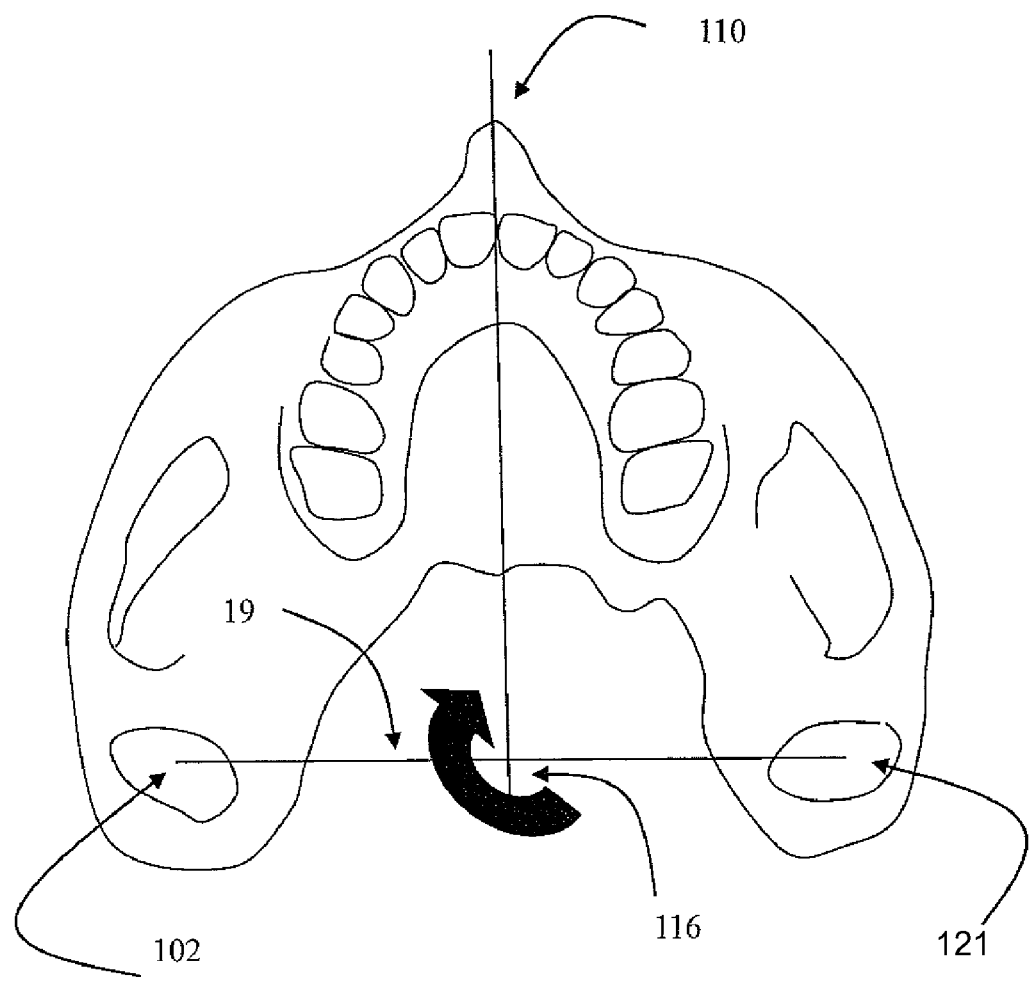
FIG. 4D is a coronal view of virtual image data that illustrates coronal rotation about a point which is the center of a rotational axis.

FIG. 4D is a coronal view of the virtual data of the patient identifying the coronal rotation about the point 116 which is the center of the rotational axis 19, which may be a line connecting the anatomic fossae 102, 121.

Figure 5A:
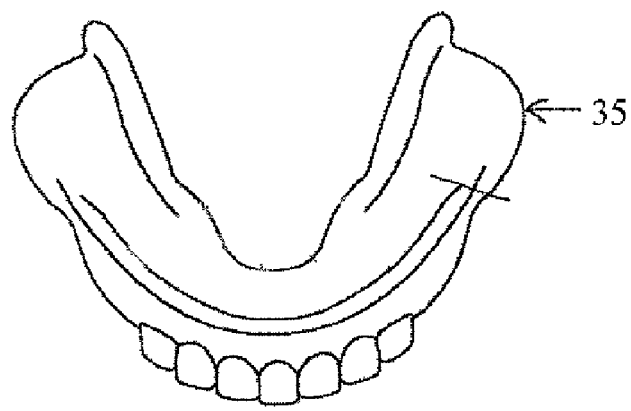
FIG. 5 illustrates a complete denture, a dental cast attached to the denture, a vacuum formed template, and a template filled with cured material to create a replica of a denture.
Figure 5B:
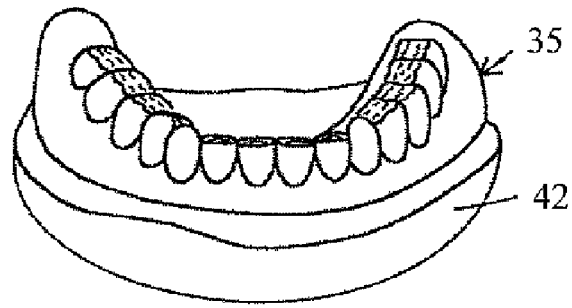
Figure 5C:
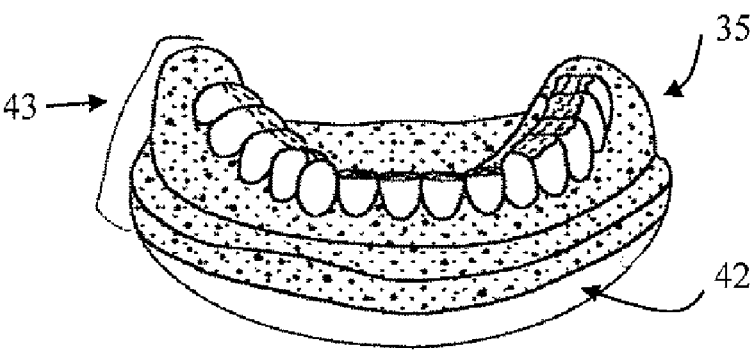
Figure 5D:
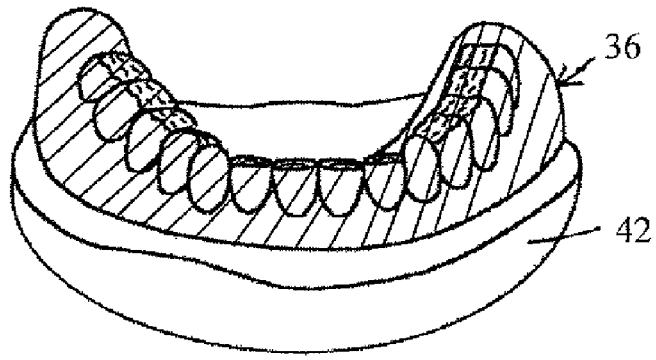

FIG. 5A illustrates a complete denture 35 after the CT scan has been made. In FIG. 5B the inside of the denture 35 is filled with dental stone to record the shape of the patient's soft tissue and to create a dental cast 42. FIG. 5C illustrates vacuum formed material 43 placed over the patient's denture to record the shape of the denture and create a replica of the denture. FIG. 5D illustrates the vacuum formed template filled with a curable material 36 to reproduce the shape of the denture. Such procedures are described in more detail in U.S. Pat. No. 7,322,824, of which Applicant is the sole inventor.

In some embodiments, the denture is a physical object that correlates with the virtual image of the teeth as shown in relation to FIG. 4. It should also be understood that the orientation of the upper denture with regards to the three non-linear radiographic markers is known, irrespective of whether or not dentition is imaged using radiographic or non-radiographic methods.

Figure 6:
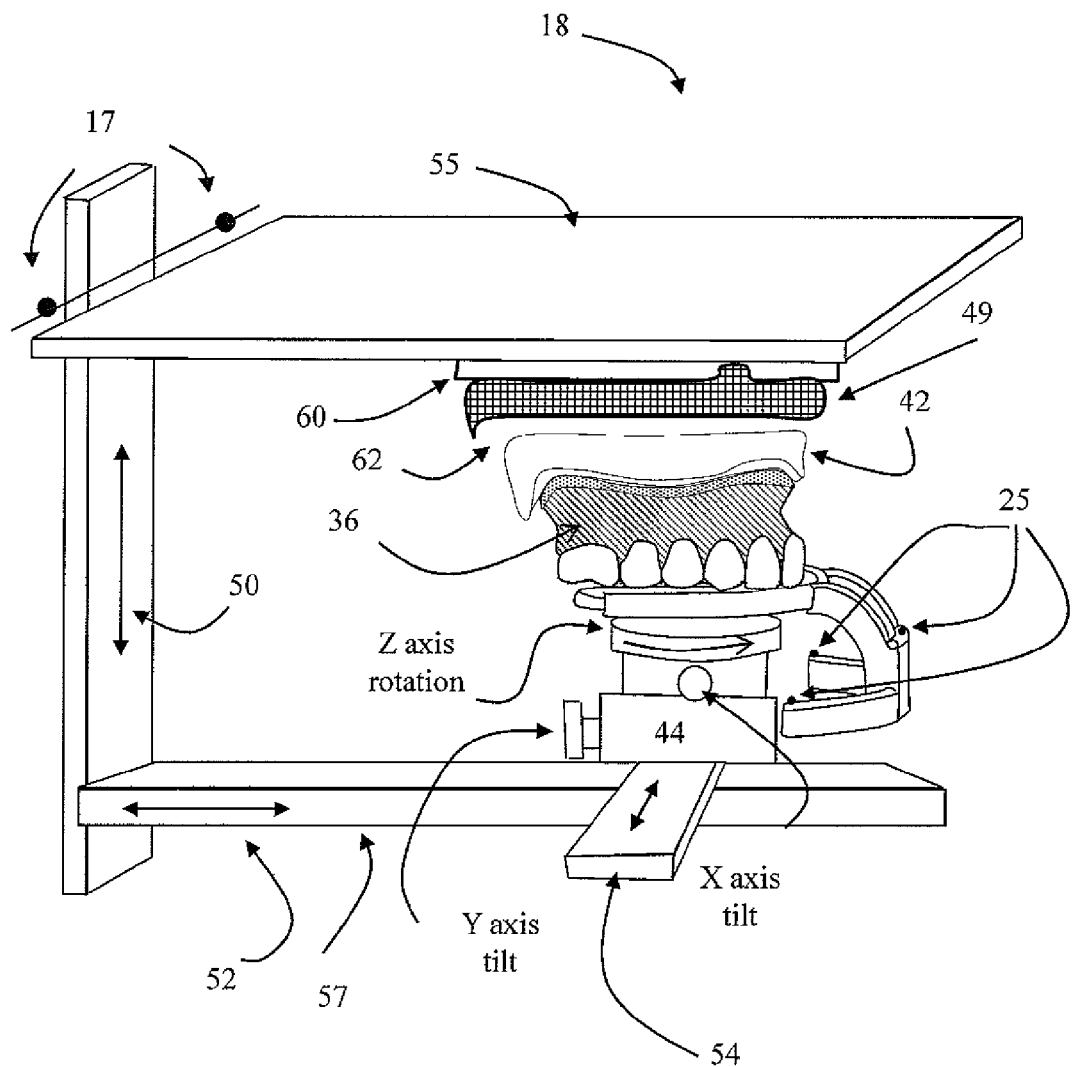
FIG. 6 shows a mechanical device for positioning the CT bite plate and upper denture/cast in the same relationship to the rotational centers as recorded in the CT image.

FIG. 6 illustrates a device 18 for positioning the dental cast or denture 36 in the precisely corresponding relationship to the rotational axis of the patient. This eliminates the need for a face bow and allows the completed computer generated prosthesis to be placed in an articulator for physical evaluation. The CT scan image data is used to determine the positional relationship of the three radiographic markers 25 and rotational centers in the virtual image. These positional relationships are then reproduced for the physical models using simple trigonometric functions. Rotational centers 17 are located in relation to the physical positioning device. In some embodiments, motion of the bottom portion 57 of the positioning device 18 may be tracked, such that the relative positions of the top portion 55 and bottom portion 57 of the device are known. In some embodiments, the CT bite plate 12 may be attached to the bottom portion 57 of the positioning device 18 in a known and reproducible manner. Positioning of the radiographic markers 25 with respect to the bottom portion 57 of the device is therefore also reproducible and known. In that light, the position of the radiographic markers 25 and denture 36, or dental cast, are known with respect to the bottom portion 57 of the device, and the position of the mounting plate 49 is known with respect to the top portion 55 of the device 18, and thus the relative positions of the radiographic markers 25, denture 36 and mounting plate 49 are all known and can be tracked as the jig 44 is moved. In addition, the position of the radiographic markers 25 are known with respect to the rotational centers 17 in virtual space. Therefore, physical components on the device 18, including the mounting plate 49, denture 36 and radiographic markers 25, can all be positioned with respect to the virtual image data of the patient's upper teeth and upper bony structures and to reference points on the virtual articulator. Furthermore, the mounting plate 49 may, in some embodiments, have a known orientation to the mechanical fossae of an actual physical articulator when mounted in an actual physical articulator. In some embodiments, the mounting plate 49 may be constructed such that it may be attached to and removable from the top portion 55, or alternatively, mounting plate 49 and top portion 55 may be removable from the positioning device together.

The CT bite plate 12 and upper or lower cast/denture 36 is attached to a jig 44 that allows for movement around a multiple axes. The jig rotates the CT bite plate 12 about the Z axis and allows tilting about the X and Y axis. This makes it possible to orient the CT bite 12 in the same angulations as existed in the CT scan or any position that is needed for the diagnostic process. The linear slides allow movement 54, 52, 50 along the X, Y, and Z axes, respectively. After the CT bite plate 12, denture replica 36 and cast 42 are positioned correctly, the cast is joined to the mounting plate 49. In some embodiments, movements of the jig may be accomplished manually by an operator. In some embodiments, movement of the jig maybe accomplished in an automated manner, such as by computer control. An operator, therefore, can maneuver the mounting plate 49 in any desired orientation with regards to other structures shown in FIG. 6. In some embodiments, the mounting plate 49 would be oriented with regards to the cast 42 such that when the mounting plate is removed and placed on an actual physical articulator, it is in a desired orientation. Such a desired orientation may, for example, orient the dental cast 42 with regards to the mechanical fossae. In some embodiments, the mounting plate 49 and cast 42 are fixed in a desired orientation by adding an acceptable fixing agent or glue, including for example mounting stone to gap 62. Mounting stone may be, for example, a fast setting gypsum-based material with minimal expansion, or other suitable material. In some embodiments, this allows the cast 42 to be transferred to a mechanical articulator, thus eliminating the need for a face bow.

Figure 7:
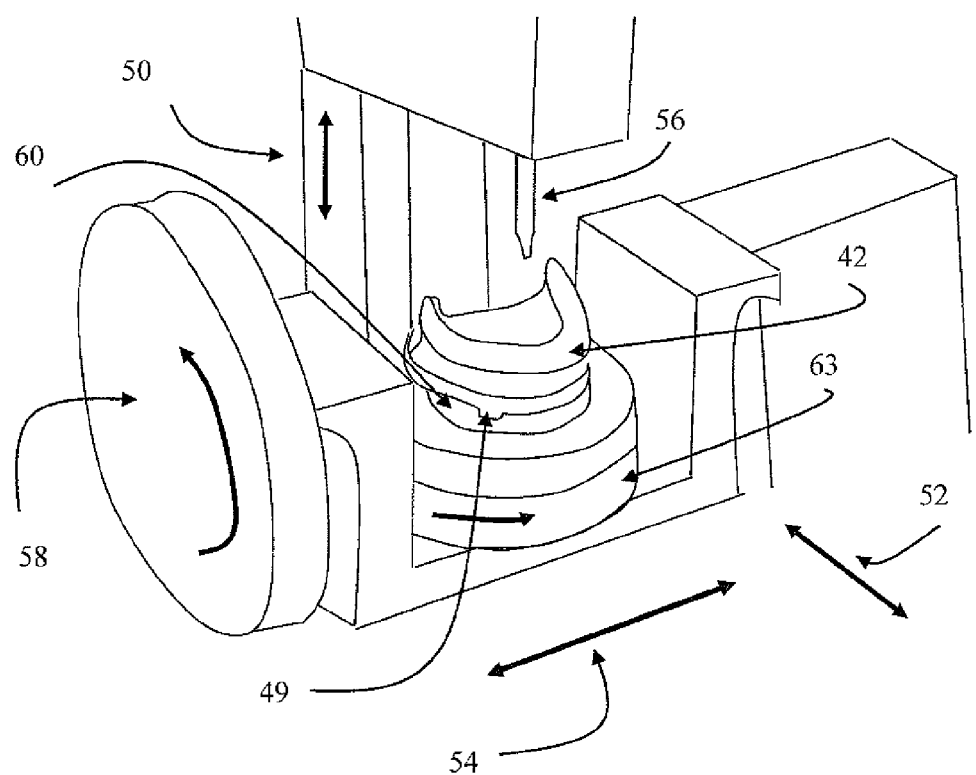
FIG. 7 illustrates a five-axis mill used to create bores in the dental cast to position guide tubes.

FIG. 7 is an illustration of a five-axis mill used to create bore holes in a dental cast 42 in the correct positions in relation to the virtual model. The mill allows for linear movement 54, 52, 50 along the X, Y, and Z axes, respectively. Rotational motion 63 is capable around the Z axis, and rotational motion 58 is capable about the X axis. A magnetic receiver 60 holds the mounting plate 49 and cast 42 in the proper orientation with respect to the machine tool 56.

Figure 8:
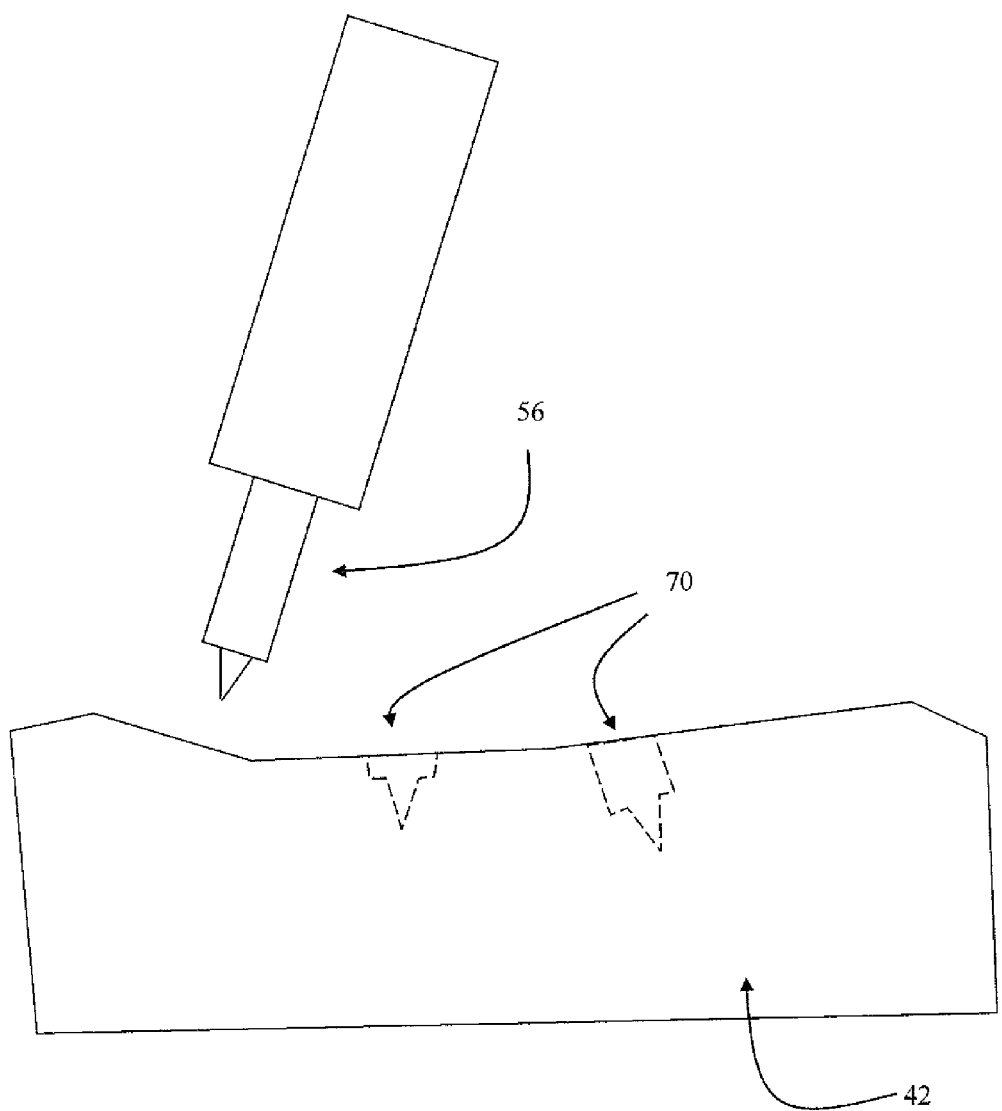
FIG. 8 illustrates the tool of a five-axis mill and bore holes in a dental cast.

FIG. 8 shows the machine tool 56 and bore holes 70 created in the dental cast for placement of guide tubes.

Figure 9:
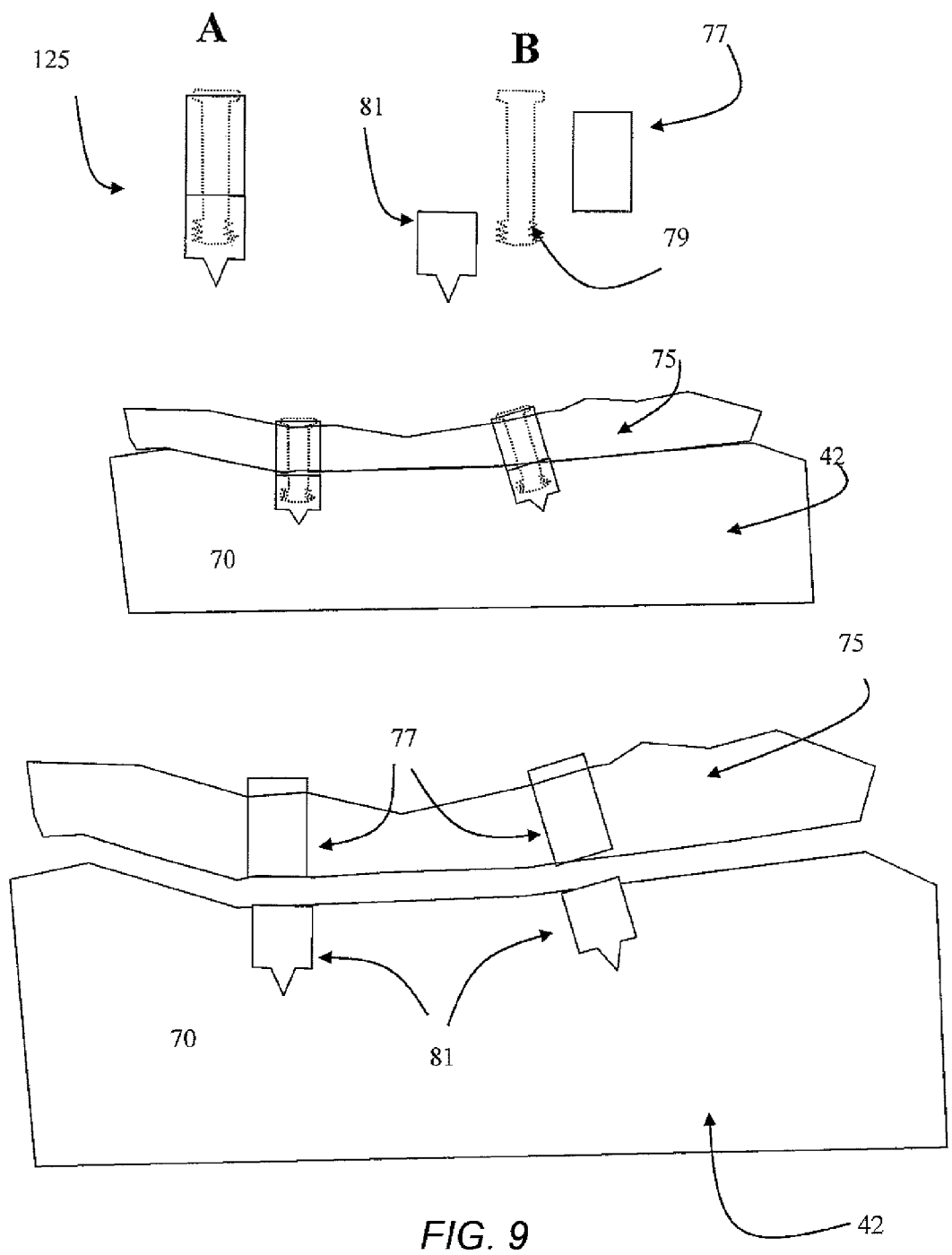
FIG. 9 is an illustration of a three-piece device for positioning guide tubes in the correct position on a dental cast.

FIG. 9 illustrates a tube retaining device 125 for positioning guide tubes in the bore holes and allows for the removal of the guide tubes and template from the cast even though the tubes are at divergent angles. FIG. 9A illustrates the tube retaining device 125 screwed together. FIG. 9B illustrates an exploded view of the tube retaining device 125 with the retaining screw 79, guide tube 77 and bore receiver 81. The bore receiver 81 is cemented into the bore holes created with the five-axis mill to record the exact position and angle for placing a specific implant from the CT imaging and planning process. The bore receiver has a threaded internal bore hole that matches the retaining screw 79. Next, the guide tube 77 and retaining screw 79 are attached to the bore receiver 81. Acrylic resin 75 or other types of curable or thermoplastic materials are then placed on the cast 42 and around the guide tubes 77 to record their position. After the resin has cured, the retaining screws 79 are removed and the surgical template 75 is separated from the cast 42.

Although the foregoing specific details describe certain embodiments of this invention, persons reasonably skilled in the art will recognize that various changes may be made in the details of this invention without departing from the spirit and scope of the invention as defined in the appended claims and considering the doctrine of equivalents. Therefore, it should be understood that this invention is not to be limited to the specific details shown and described herein.

What is claimed is:

1. A method of positioning a model of a patient's dentition comprising:
   receiving first digital data representative of a patient's dentition;
   receiving CT data of the patient's fossae and a CT bite plate having three or more non-linear radiographic markers, said dentition being oriented with respect to said fossae in an actual orientation, said CT bite plate being engaged with said dentition;
   creating a virtual model of said dentition, said fossae, and said radiographic markers from said first digital data and said CT data, said virtual model comprising a virtual representation of said dentition, a virtual representation of said fossae, and a virtual representation of said radiographic markers, wherein said virtual representation of said dentition is oriented with respect to said virtual representation of said fossae in a virtual orientation, said virtual orientation being substantially the same as said actual orientation;
   mounting an actual model of said dentition in a positioning device using said CT bite plate, said positioning device comprising a removable mounting plate, said mounting plate being attachable to an actual articulator in a known orientation;
   orienting said actual model of said dentition with respect to said mounting plate in said positioning device;
   attaching said actual model to said mounting plate;
   removing said actual model and said mounting plate from said positioning device; and
   positioning said actual model in said actual articulator using said mounting plate;
   wherein said virtual model comprises the locations of the anatomic fossae and an incisor in the upper teeth and upper boney structures of the patient; and
   wherein said locations are used to calculate the precise corresponding position of mechanical fossae and the vertical position of an incisal pointer in said actual articulator.

2. The method of claim 1 wherein said CT bite plate comprises bite registration material to record indentations of upper and lower teeth of said dentition.

3. The method of claim 1 further comprising acquiring a second image wherein said CT bite plate is disposed outside of the patient's mouth to record the patient's occlusal and tissue surfaces.

4. The method of claim 1 wherein said dentition comprises a denture which is filled with impression material to record the precise contour of soft tissue of the patient's jaw and the shape of the denture.

5. The method of claim 1 wherein said virtual model comprises a denture, said radiographic markers, and rotational centers and axis of rotation of the patient's jaw.

6. The method of claim 5 wherein said rotational centers are identified using 3D data comprised of one or more of the skin and tragus of the ear, external auditory meatus, condylar head, condylar fossae, and actual digital recording of points on said axis.

7. The method of claim 1 wherein said virtual model comprises the locations of the nasion point and the anterior nasal spine point.

8. The method of claim 1 wherein said dentition comprises a denture and wherein the inside of said denture is filled with dental stone to record the shape of the patient's soft tissue and to create a dental cast.

9. The method of claim 1 wherein said dentition comprises a denture and further comprising using vacuum formed material placed over said denture to record the shape of the denture and create a replica of the denture.

10. The method of claim 1 wherein said actual model comprises a dental cast and wherein using said virtual model to position the dental cast in the articulator comprises:
    determining the positional relationship of the radiographic markers and a virtual representation of rotational centers;
    attaching said CT bite plate and said dental cast to a jig; and
    moving said jig as necessary to orient the radiographic markers in the same angulations as found in said virtual model.

11. The method of claim 1 wherein said dentition comprises natural teeth and further comprising evaluating an aesthetic appearance of the patient prior to removal of any of said natural teeth and using virtual techniques to plan replacement teeth, shape the supporting bone, place implants, construct surgical guides and construct an immediate prosthesis.

12. The method of claim 1 wherein said dentition comprises natural teeth and further comprising using said virtual model to position virtual artificial teeth in proper spatial orientation to the patient's supporting tissues, any of said existing natural teeth and the patient's opposing arch.

13. The method of claim 1 further comprising using said virtual model to determine an ideal position to place implants in supporting bone.

14. The method of claim 1 wherein said actual model comprises a dental cast and further comprising using said virtual model and said dental cast positioned in said articulator to make a dental device.

15. The method of claim 14 wherein said dental device is selected from a surgical drill guide, an immediate denture, and an immediate load prosthesis.

16. The method of claim 1 wherein said dentition comprises removable dentures and further comprising using the removable dentures to record the shape of soft tissue and the spatial orientation of the dentures to the supporting tissue to create surgical guides for placing one or more dental implants.

17. The method of claim 16 wherein a five axis mill is used to create a bore hole in a dental cast in a correct position in relation to said virtual model.

18. The method of claim 14 further comprising using computer techniques selected from computer milling and layered manufacturing.

19. The method of claim 1 further comprising collecting a non-radiographic image of a patient's denture or any of the patient's existing natural teeth.

20. The method of claim 1 wherein said first digital data is acquired radiographically.

21. The method of claim 1 wherein said first digital data is acquired non-radiographically.

22. A method of positioning a model of a patient's dentition comprising:
    receiving first digital data representative of a patient's dentition;
    receiving CT data of the patient's fossae and a CT bite plate having three or more non-linear radiographic markers, said dentition being oriented with respect to said fossae in an actual orientation, said CT bite plate being engaged with said dentition;
    creating a virtual model of said dentition, said fossae, and said radiographic markers from said first digital data and said CT data, said virtual model comprising a virtual representation of said dentition, a virtual representation of said fossae, and a virtual representation of said radiographic markers, wherein said virtual representation of said dentition is oriented with respect to said virtual representation of said fossae in a virtual orientation, said virtual orientation being substantially the same as said actual orientation;
    mounting an actual model of said dentition in a positioning device using said CT bite plate, said positioning device comprising a removable mounting plate, said mounting plate being attachable to an actual articulator in a known orientation;
    orienting said actual model of said dentition with respect to said mounting plate in said positioning device;
    attaching said actual model to said mounting plate;
    removing said actual model and said mounting plate from said positioning device; and
    positioning said actual model in said actual articulator using said mounting plate;
    wherein said virtual model comprises the locations of the nasion point and the anterior nasal spine point; and
    wherein said locations are used to rotate the frontal plane of the articulator around the anterior nasal spine to position the nasion in a vertical position directly over the anterior nasal spine.

23. A method of positioning a model of a patient's dentition comprising:
    receiving first digital data representative of a patient's dentition;
    receiving CT data of the patient's fossae and a CT bite plate having three or more non-linear radiographic markers, said dentition being oriented with respect to said fossae in an actual orientation, said CT bite plate being engaged with said dentition;
    creating a virtual model of said dentition, said fossae, and said radiographic markers from said first digital data and said CT data, said virtual model comprising a virtual representation of said dentition, a virtual representation of said fossae, and a virtual representation of said radiographic markers, wherein said virtual representation of said dentition is oriented with respect to said virtual representation of said fossae in a virtual orientation, said virtual orientation being substantially the same as said actual orientation;
    mounting an actual model of said dentition in a positioning device using said CT bite plate, said positioning device comprising a removable mounting plate, said mounting plate being attachable to an actual articulator in a known orientation;
    orienting said actual model of said dentition with respect to said mounting plate in said positioning device;
    attaching said actual model to said mounting plate;
    removing said actual model and said mounting plate from said positioning device; and
    positioning said actual model in said actual articulator using said mounting plate;
    wherein said virtual model comprises the locations of the nasion point and the anterior nasal spine point; and
    wherein said virtual model is used to record the location of the coronal rotation point at the intersection of a line connecting the anatomic fossae and a line intersecting the aforementioned line and the anterior nasal spine point.

* * * * *